US005421335A

United States Patent [19]

Wild

[11] Patent Number: 5,421,335

[45] Date of Patent: Jun. 6, 1995

[54] INTRINSICALLY COLLIMATED ULTRASONIC TRANSDUCER

[76] Inventor: John J. Wild, 4262 Alabama Ave. South, Minneapolis, Minn. 55416

[21] Appl. No.: 184,211

[22] Filed: Jan. 21, 1994

[51] Int. Cl.[6] .......... A61B 8/00

[52] U.S. Cl. .......... 128/662.03; 73/625

[58] Field of Search .......... 128/662.03, 663.01; 73/625, 626, 642, 644; 310/334, 335; 348/115; 378/205; 29/25.35

[56] References Cited

U.S. PATENT DOCUMENTS

| | | | |
|---|---|---|---|
| 3,696,479 | 10/1972 | Dias | 29/25.35 |
| 4,198,654 | 4/1980 | Coulomb | 348/115 |
| 5,122,993 | 6/1992 | Hikita et al. | 128/662.03 |
| 5,123,418 | 6/1992 | Saurel et al. | 128/662.03 |
| 5,305,756 | 4/1994 | Entrekin et al. | 128/662.03 |
| 5,311,568 | 5/1994 | McKee, Jr. et al. | 378/205 |

*Primary Examiner*—George Manuel
*Attorney, Agent, or Firm*—James R. Owayna

[57] ABSTRACT

An improved piezo-electric transducer to provide a maximal transmission of ultrasonic energy into and from human and animal tissues for the determination of abnormalities eliminating the necessity of collimating accessories at transducer level, which accessories result in avoidable energy transmission and receipt losses. An ICT (Intrinsically Collimated Transducer) provides parallel beam transmission with the emitted beam focussed at infinity. The transducer affords an intrinsically collimated beam of energy to insure a most favorable diagnostic approach to detection of tissue abnormalities. A thin piezo-electric, ceramic, member is provided with one side having a plurality of isolated electrodes which are commonly or individually connected by means of a flexible, compressible, elastomeric, energy conducting membrane or means such as highly conductive metals, though relatively inflexible when compared to elastomers are relatively flexible as compared to solid metals. The plurality of isolated, conductive electrodes provide a plurality of energy conductive paths through the transducer which results in parallel sonic energy minibeams being emitted from the frontal face of the transducer. These electrodes function to receive return energy upon echo from the tissue.

1 Claim, 4 Drawing Sheets

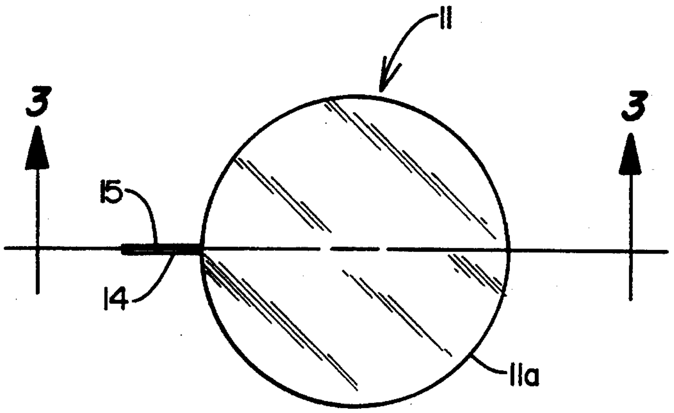
FIG. 1
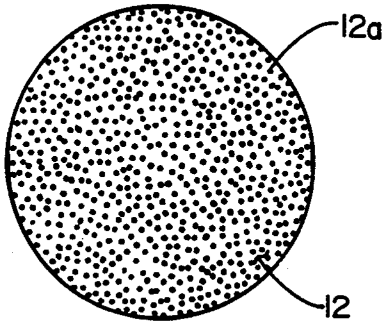
FIG. 2
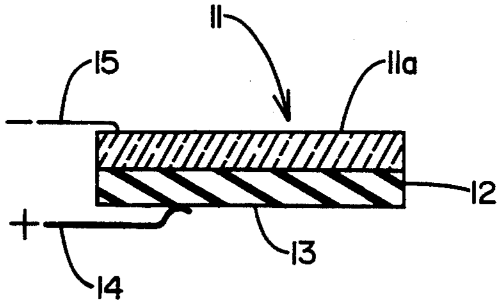
FIG. 3a
FIG. 3b
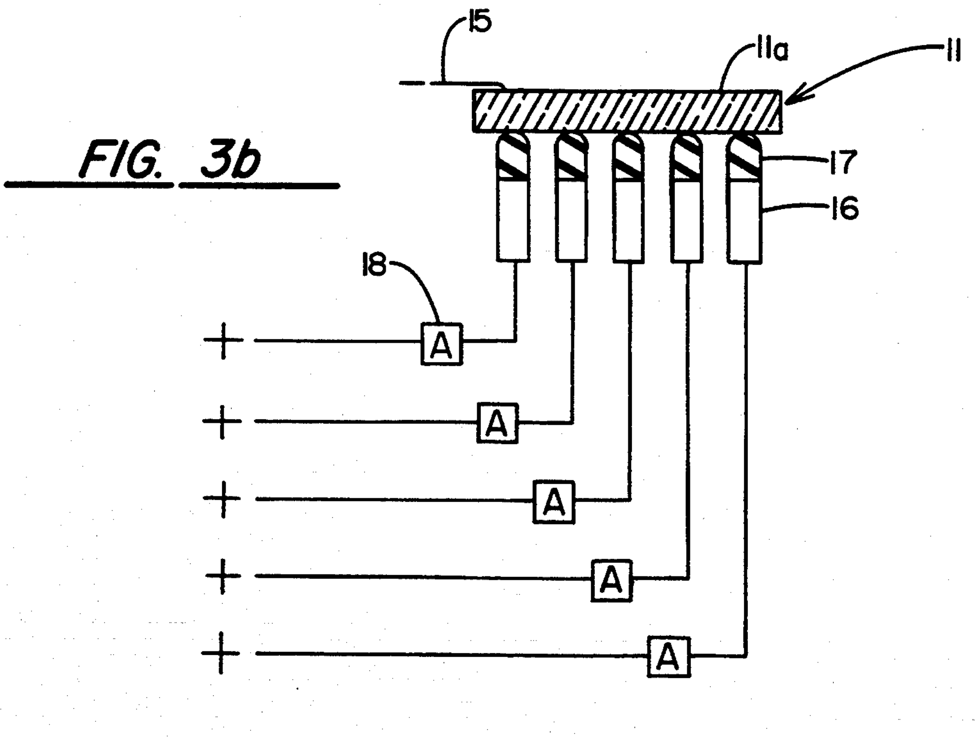

INTRINSICALLY COLLIMATED ULTRASONIC TRANSDUCER

RELATED APPLICATIONS

There are no applications by applicant currently on file in the United States Patent Office related to this application.

FEDERAL SPONSORSHIP

This invention is not made under any Federally sponsored research or development arrangement nor under any other independently sponsored research and development arrangement.

1. Field of the Invention

This invention relates generally to ultrasonically energized transducers and more particularly to a piezo-electric ceramic plate transducer having a plurality of electrodes on the rear surface thereof to provide a plurality of energy transmission and receiving points on the frontal surface thereof to produce an intrinsically collimated beam particularly directed to the detection of tissue abnormalities including tumors such as cancer.

2. Summary of the Invention

A piezo-electric medium, such as ceramic, transducer which provides for maximum and efficient energy transmission into and from human as well as animal tissues for the detection of tissue abnormalities including cancerous tumors. The transducer provides an intrinsically collimated beam avoiding the need for external collimating elements such as lenses or the like which elements reduce transmitted and received energy.

The transducer provides for parallel beam transmission and receipt which thereby provides intrinsic focussing of the beam at infinity within a useful area and range. This beam possesses cross-sectional integrity and azimuthal or lateral resolution.

The transducer provides a plurality of isolated conductive points on a first or rear side of a crystal which points, in the preferred embodiments, are commonly or selectively, singularly connected by a flexible, resilient, energy conducting membrane or relatively soft, metallic plate, to the source of ultrasonic energy. The plurality of isolated conductive points provide a multiplicity of energy conducting points and thus paths through the ceramic plate to result in multiple mini-beams being emitted from the frontal surface of the transducer at a multiplicity of exit areas. As the device may be operated as an emitter and a receiver, or both, these points function to transmit and receive energy, upon echo, from the tissue.

Though the plurality of beams together form a composite beam, which operates as a single beam consisting of a composite plurality of energy segments all of which emanate from the transducer as unidirectional energy beams and all of which are intrinsically focused at infinity.

The thickness of the piezo-electric plate member in relation to the conductive path therethrough provides what is termed a diameter to length ratio, with the diameter being the dimension of the energy path through the member and the length being the thickness of the member. This ratio, when properly calculated and presented eliminates conduction between energy paths through the crystal and prevents internal interference. Spectral purity then is assumable and electronic noise is reduced or totally eliminated.

In the present invention, the energy receiving side of the ceramic plate is divided into a number of separate electrodes which are coupled, in the preferred form, to the energy source through a relatively thin, common or individual, conductive rubber or elastomeric member or members or similarly through a relatively soft metallic member or members. Similarly, the separate electrodes may be individually coupled in the same manner. The ultrasonically energized transducer functions uniquely to produce a parallel, collimated beam of great signal sensitivity throughout the length of the beam.

BACKGROUND AND OBJECTS OF THE INVENTION

Applicant's novel approach to acoustic beam modification arose in response to the very poor sonic beam directivity of piezo-electric, such as ceramic, transducers for detection of differential diffuse backscatter from small volumns of abnormal cells surrounded by normal cellular structures as the same are now known. At high frequencies, necessary for small cellular volume detection, certain basic acoustic limitations necessitate the maximum possible input and output of sonic energy from such a pulse-reflective system for early stage cancer detection. Properties of the acoustic system must be fine-tuned to detect and differentiate the very weak sonic energy signal contrast between normal and tumorous tissue.

The inventor has confirmed the existence of such signal differences between between tumors and surrounding tissues having forecast this possibility by quantitative studies of comparable time-amplitude graphs of normal and tumorous tissues.

This work was initially done with air-backed quartz transducers working in the near field. Ceramic tranducer materials offered much greater acoustic sensitivity but possessed serious limitations in the beam profile. This limitation was initially overcome by externally focussing the beam with acoustic lenses which resulted in loss of maximum degree of target detectability of diffuse back-scatter which has been found clinically necessary to achieve maximum target sensitivity.

X-cut quartz piezo-electric transducer plates can be designed to produce a highly directive beam of ultrasonic energy, operating as plane piston radiators to produce Gausian Apodization Beams. The quartz Gausian Beam is not uniformly sensitive axially and produces various degrees of maximum and minimum intensity nodes along its length.

Ceramic plates were selected as being more suitable than quartz for the purpose of target identification in human and animal tissues containing abnormal, irregular, disordered cellular structures such as tumors, some of which produce diffuse back-scattered reflection of sonic energy. Ceramic plates were found to be deficient directionally when operated as a plane piston. Current practices use focusing by acoustic lenses to correct this deficiency with resultant loss of maximum sensitivity to clinically desirable, smallest levels of diffuse, back-scattered signal content.

The present invention has solved the problem of poor axial beam directivity of ceramic transducer plates without reducing target sensitivity which are naturally of a much higher order in revealing diffuse back-scattered sonic energy than that of X-cut quartz.

With applicant's invention, the energy receiving or energy input side of the plate has been divided into a number of separate electrodes. When coupled with a suitable electrode backing such as a conducting rubber or elastomeric member, rigid plate, or preferably a relatively soft metallic plate or individual conductor, the electrically energized transducer functions uniquely to produce a parallel beam of uniform intensity throughout the useful range of the beam, with integrity throughout the cross section of the beam and with azimuthal consistency. Applicant has also found the beam to be steerable by selective energization of the electrodes through a variety of excitement modes including integrated ciruit amplifiers with controlled, sequential or simultaneous stimulation of the electrodes.

Such an intensity-uniform beam of ultrasonic energy has been shown experimentally to detect far more backscatter energy from mammalian tissue. The present state-of-the-art knowledge has sacrificed maximum tissue signal sensitivity in a perceived quest by some designers for essential, including azimuthal or lateral, signal clarity. This developmental trend has not yet resulted in realization of the full potential of ultrasound for tumor detection and diagnosis.

It is therefore an object of the applicant's invention to provide an intrinsically collimated, ultrasonic transducer which provides for a plurality of separately emitted beams acting as a single beam focussed at infinity.

It is a further object of the applicant's invention to provide an intrinsically collimated, ultrasonic transducer which eliminates the requirement of focussing elements for image clarity by obtaining a collimated, parallel beam of energy of total transducer area for the detection of very small cellular tissue abnormalities as compared to a narrow, point focussed beam..

It is a further object of the applicant's invention to produce an intrinsically collimated, ultrasonic transducer having a plurality of electrodes with a conducting, flexible member providing ultrasonic energy to each of its separate electrodes.

It is still a further object of the applicant's invention to produce an intrinsically collimated, ultrasonic transducer which provides a maximal, desired, low energy loss energy transmission at transducer level, into and from human tissues.

It is yet a further object of the applicant's invention to provide an intrinsically collimated ultrasonic transducer which provides a new and novel means for more complete detection and certain, accurate diagnosis of tissue abnormalities.

These and other objects of the applicant's invention will more fully appear from a consideration of the accompanying drawings and description of the invention.

DESCRIPTION OF THE DRAWINGS

FIG. 1 is a view of the front of a ceramic transducer embodying the concepts of applicant's invention;

FIG. 2 is a view of the rear of the transducer particularly illustrating the conductive points of the same;

Figure 4:
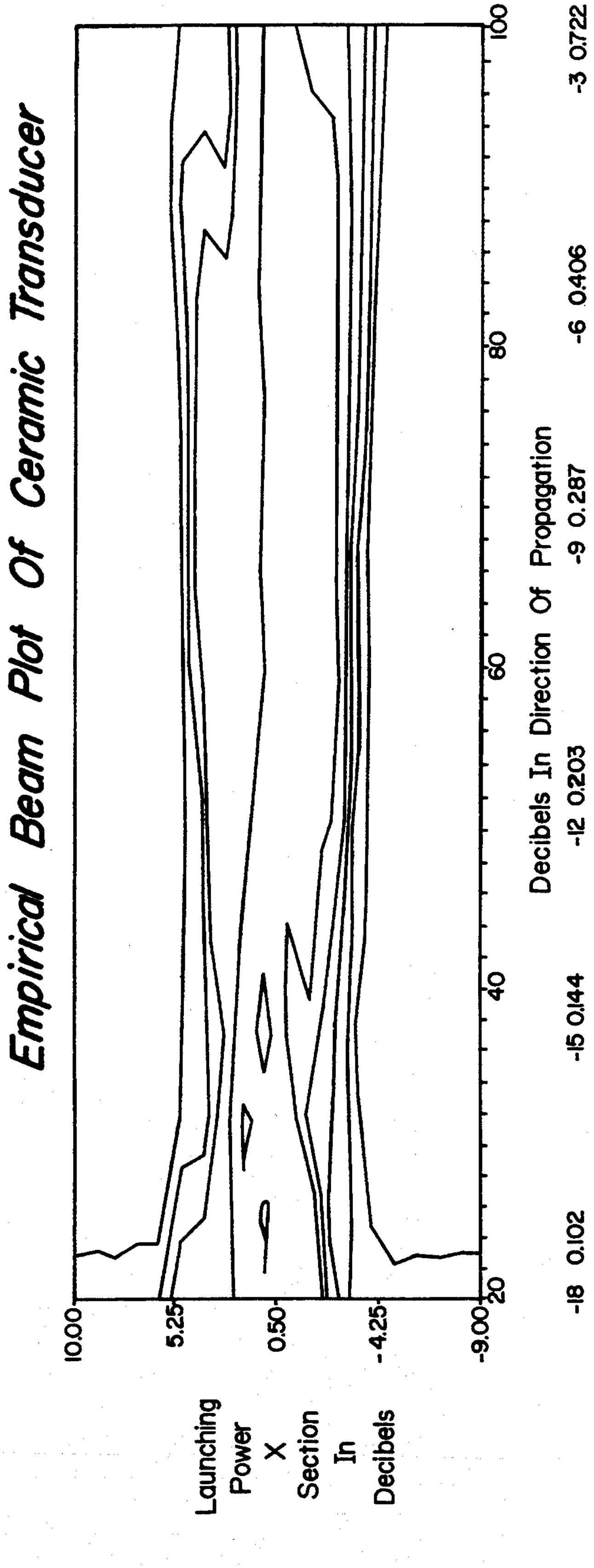
Figure 6:
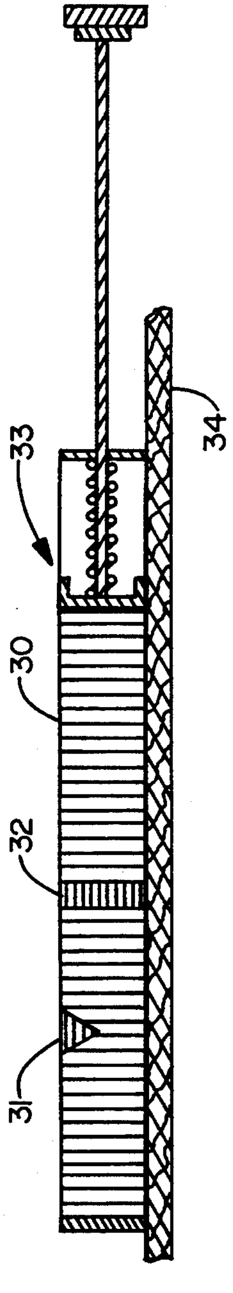
Figure 5:
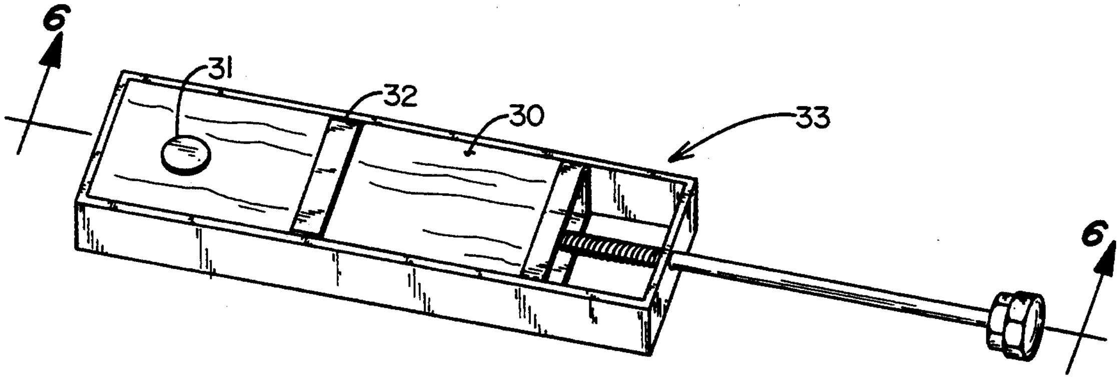
Figure 7:
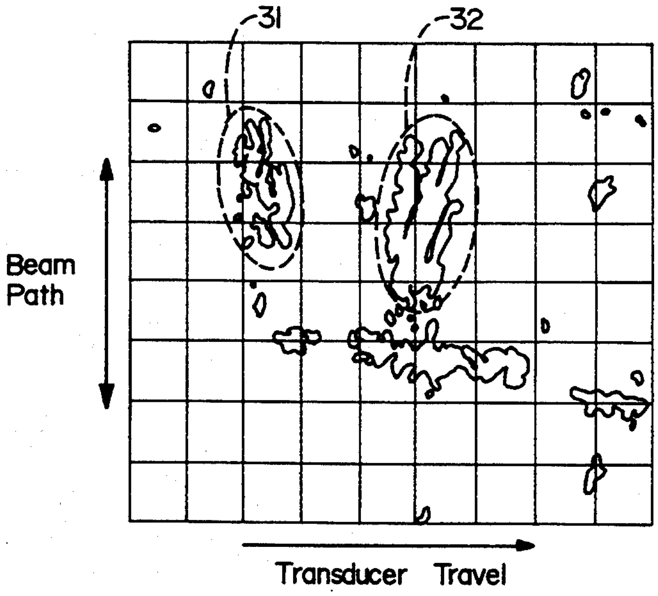

FIG. **3*a* is a first cross section taken substantially along Line 3—3 of FIG. 1** illustrating a first form for energizing the trasnsducer and the conductive points thereof;

FIG. **3*b* is a second cross section taken substantially along Line 3—3 of FIG. 1** illustrating a second form for energizing the transducer and the conductive points thereof;

FIG. 4 is an Empirical Beam Plot of the beam emitted from the energized transducer;

FIG. 5 is a perspective view of a testing arrangement utilizing a meat sample with ectopic implants therein to test the effectiveness of the beam transmission and receptiveness to tissue abnormalities;

FIG. 6 is a section taken substantially along Line 6—6 of FIG. 5;

FIG. 7 is an illustration of the energy reception from the testing arrangement for the meat and tissue sbnormalities of FIGS. 5 and 6; and, FIGS. **8*a* and 8*b*** are illustrations of the energy receptions and thus results of the application of Applicant's concepts on a normal and an "inflamed nipple" of a woman's breast to reveal the presence of a cancerous tissue tumor.

DESCRIPTION OF PREFERRED FORMS OF THE INVENTION

As illustrated in the accompanying drawings, the ceramic transducer embodying the concepts of the applicant's invention is generally designated 11. The frontal surface of the transducer 11 is designated **11*a* with the rear surface thereof designated 12. The particular shape of the crystal 11** is immaterial to the function thereof and may be circular, rectangular or of any given form. The actual ceramic body is of minimal thickness such that the path for the ultrasonic energy passing therethrough will be short in nature.

As particularly illustrated in FIG. 2 the energy receiving side 12 of the transducer 11 is provided with a plurality of randomly scattered particulate electrodes **12*a***.

As illustrated in the cross sections of FIGS. **3*a* and 3*b*, two methods for energizing the electrodes 12*a*** are provided.

In the first form of transducer energization of FIG. **3*a*, the electrodes 12*a* are commonly energized through a generally flat, total surface covering, conductive, flexible rubber or elastomeric member 13 which is energized through spring contact 14. Similarly, though this member 13 is cross hatched for an elastomer, it should be obvious that this member may also be provided as a relatively soft metallic or alloy material which will provide conductivity and flexibility. The frontal surface 11*a* of the crystal 11 is, through conductor 15, oppositely charged with respect to the rear suface 12**.

In the second form of electrode energization of FIG. **3*b*, the electrodes 12*a* are individually energized through indivdual conductors 16, each of which is provided with a frontally located, conductive, flexible rubber or elastomeric member 17. Similarly, as described above, these individual conductors may be provided of a relatively soft metallic or alloy material without departing from the scope of the invention. Similarly, each of the conductors may be spring loaded in energy transferring relation with the various electrodes. Again, the frontal surface 11*a* of crystal 11 is oppositely charged through conductor 15. Amplification or tuning of conduction may be provided through amplifiers 18 or the like. Similarly, applicant has found that it is possible to "steer" or otherwise direct and control the collimated beam emitted from the frontal surface 11*a* of the crystal 11 by selectively or sequentially energizing the electrodes 12*a***.

A primary aspect of the energization of the transducer 11 is to provide for maximum ultrasonic energy transmission and receipt at the optimal natural frequency of the ceramic plate 11. With such a relationship the transducer 11 and the electrodes **12*a***, the ultrasonic paths through the transducer provide, in effect, a plurality of edge mounted, singular transducer elements, each of which provides a particulate ultrasonic beam to the tissues being interrogated. As the ceramic plate acts as a transducer, the interrogated tissue reflects ultrasonic energy back to the plate, again at the optimum, overall frequency of the ceramic plate, for maximum ultrasonic energy transmission and reception and thus the most efficient tissue interrogation.

In actuality even though the paths through the transducer are individual, the beam emitted therefrom provides an intrinsically collimated beam of energy in which the collimated condition insures a maximum amount of energy transmission and receipt to thus insure a maximum applicable diagnostic approach to detection of tissue abnormality. The exited and returning beam has cross sectional integrity and azimuthal consistency with lateral resolution which results in visually stressed representation of even the smallest tumors.

In the forms of the invention illustrated in FIGS. 3*a* and 3*b*, the connective devices from conductors 14, 16 include flexible, resilient, compressible energy conductive elements 13, 17. These conductive elements 13, 17 provide a damping connection to the device. Damping prevents mechanical "ringing" which detracts seriously from tissue interrogation and analysis appreciation. Again, this damping is available with the, above described, relatively soft, metallic connectors.

The thickness of the ceramic plate and the diameter of the energy path through the same establish what is termed the diameter/length ratio. When this ratio is low, conduction between energy paths through the plate is similarly very low to virtually eliminate internal cross path interference as energy is transmitted through the ceramic plate in both directions.

The transmission of energy from the rear connective surface of the plate to the frontal transmissive and receptive surface thereof may then be defined and designated as a straight line of such minimal length that cross transmission between energy paths is virtually eliminated. From such diameter to length ratio spectral purity is assumable.

An intensity uniform, collimated beam of ultrasonic energy has been shown to detect far more diffuse back scatter energy than either quartz crystals or other state-of-the art equipment. The back-scatter energy retrieval substantially increases the aspect of total analysis and this total tissue analysis provides for a maximum degree of tissue interrogation and thus the clinically desirable differential and revelation of minimally sized tissue abnormalities. Such a collimated beam also provides substantially constant resolution regardless of path length and allows for maximum detectability of the smallest target volume regardless of range without focussing or without concern for signal degradation attributable to non observed tissue.

With applicant's device, a selected pattern of electrodes insures smooth, uniform oscillation patterns of the transducer face at the fundamental nodal frequency to insure maximum energy transmission and receipt.

Although the beam emitted by the crystal may be defined as a plurality of beams, the beam is, in fact, a single composite consisting of a plurality of energy segments, all of which emanate from the crystal as unidirectional energy beams and all of which are focused at infinity. It is known that coherency as compared to collimation provides an energy beam in which separate beams cohere to each other and are in phase. A coherent energy beam may or may not provide a parallel combination of energy beams and normally will not achieve any far-reaching parallelism without the aid of focussing lenses which detract from or impede transmission and receipt of energy.

FIG. 4 is an empirical beam plot of applicant's ceramic transducer wherein the vertical scale represents the power at the frontal surface of the transducer and may be termed launching power for transmission of the sonic energy. The scale is in decibels. The horizontal axis of this beam plot again is measured in decibels in the direction of propogation of the beam. It should be specifically pointed out that the beam is absent of nodal points in comparison to other beams such as coherent beams which normally include a plurality of such nodal points.

As illustrated by the plot of FIG. 4, there is substantially minimal range reduction in sonic energy transmission which demonstrates the maximum efficiency of energy transmission.

FIGS. 5 and 6 illustrate the testing set up utilized by applicant in initially determining the effectiveness of his transducer. In the test, a piece of meat 30, e.g. beef steak, was implanted with two, anisotropic, cross grain abnormalities 31, 32, the same placed in a clamp unit 33 and placed on a relatively non-transmissive member 34.

The visual energy received, intensity readout from scanning the specimen with a transducer, provided with the applicant's design concepts is illustrated in FIG. 7. (The photograph from which this drawing was reproduced is available) As illustrated in FIG. 7, the implanted, anisotropic, cross-grain abnormalities 31, 32 are positively detected, clearly defined and emphasized.

With the applicant's ceramic transducer as energized by the randomly scattered particulate electrodes, an actual high contrast, black and white, instantaneous visual readout is obtained.

Figure 8A:
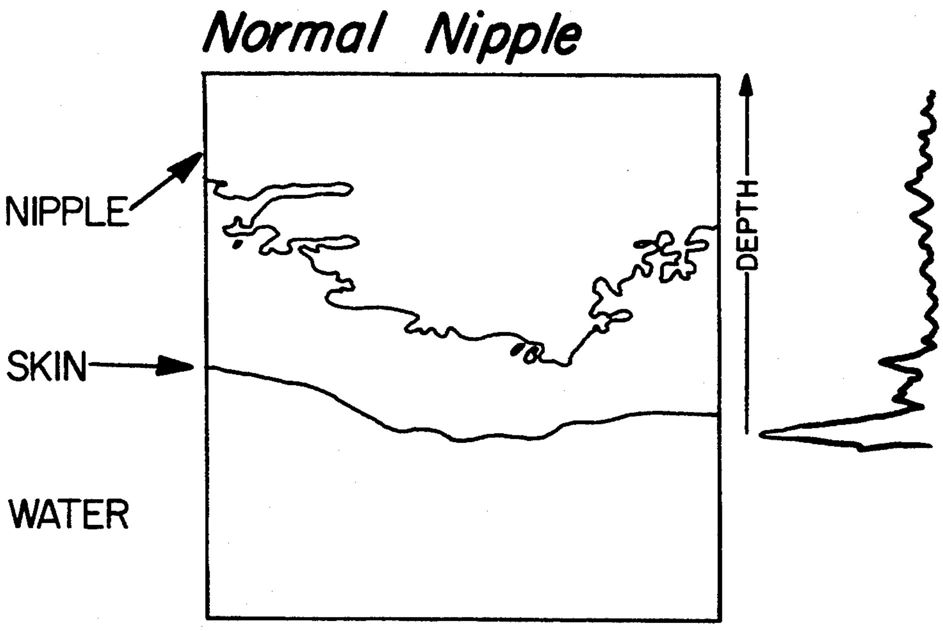
Figure 8B:
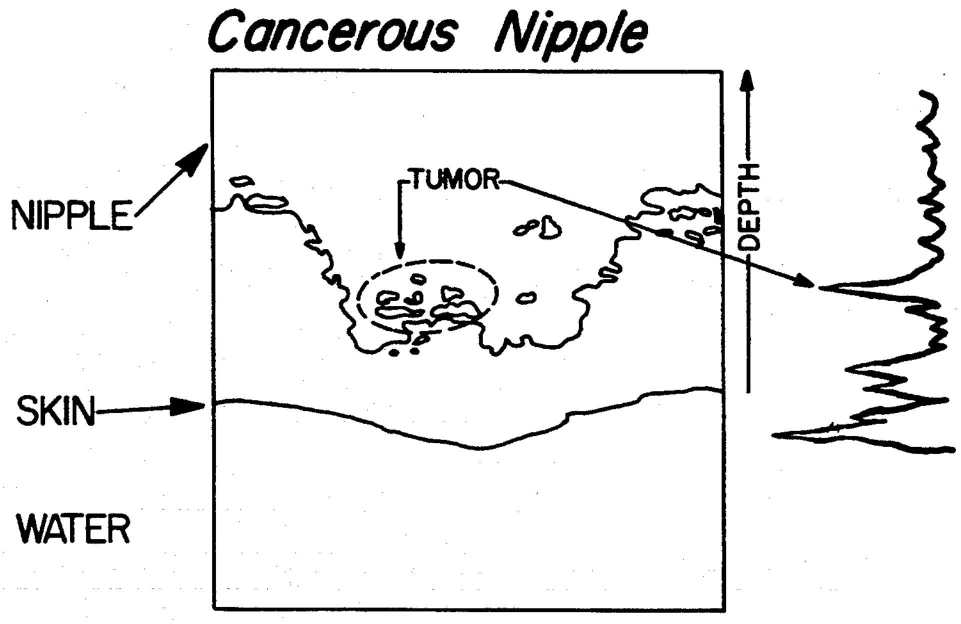

FIGS. 8*a* and 8*b* again are reproductions of photographs establishing the instant, visual readouts available with the applicant's transducer. As the nipple-areolar, central volume, is one of the sites of cancer occurrence in the human breast, this convenient volume was chosen for testing. FIG. 8*a* illustrates the ultraasonic image of tissue structure of a normal breast nipple and FIG. 8*b* illustrates that of a clinically examined breast nipple diagnosed as inflamed. The beam was directed through a water bath to pass into and through the skin and into the nipple central volume. The differences between the normal nipple and the "inflamed" nipple are easily, visually discernable by either of two ways. This is either visualized as a two dimensional image or as uni-directional amplitude modulated, graphically displayed traces seen to the right side of the immages.

Applicant has found that his transducer provides total, unselected, sonic energy retrieval without rejection or suppression of specular, specular back-scatter or diffuse back-scatter sonic energy. By processing all reflected energy, applicant provides a means for detecting relatively small volume tumors including cancerous abnormalities.

Although continual reference has been made to the transducer being ceramic, it should be obvious that the transducer is basically of a piezo-electric medium.

Again, although the applicant illustrates the utilization of his device on the human breast, it should be pointed out that the experimental work illustrated in FIGS. 5, 6 and 7 utilizes a piece of beef. Therefore the utilization of applicant's device for animals is within the scope of the invention.

The uniqueness of the applicant's transducer should be obvious to anyone skilled in the art. With such a transducer and the proper utilization of the produced, high energy transmissive and reflected, collimated beam; a tool which eliminates patient pain in clinical application and inherent dangers of X-radiation is provided. Therefore, it should be obvious that the applicant has provided a new and unique ultra-sound transducer operational at a maximum level of ultrasonic energy transmission and receipt which accomplishes the intended results through intrinsical collimation, parallel focusing of the beam within a useful area and range.

What is claimed is:

1. An ultrasonic transducer particularly arranged and constructed for detection of tissue abnormalities, including:

a. a piezo-electric plate providing a generally planar frontal surface and a generally planar rear surface;
b. a plurality of electrodes provided on said rear surface of said piezo-electric plate;
c. means for supplying ultrasonic energy to said plurality of electrodes on said rear surface of said plate wherein said means includes;
   1. separate, flexible conductive members individually contacting each of said eletrodes;
   2. separate conductors from a source of ultrasonic energy to each of said conductive members; and
   3. said separate flexible conductive members include relatively soft metallic elements and relatively soft metallic .alloys whereby said piezo electric plate will emit an intrinsically collimated beam from the frontal surface thereof when energized with ultrasonic energy.

* * * * *